(12) United States Patent
Badwan et al.

(10) Patent No.: US 6,242,444 B1
(45) Date of Patent: Jun. 5, 2001

(54) COMPOUNDS AND PHARMACEUTICAL COMPOSITIONS CONTAINING THE SAME

(75) Inventors: Adnan Ali H. Badwan; Mustafa M. M. El Abadelah, both of Amman (JO)

(73) Assignee: The Jordanian Pharmaceutical Manufacturing and Medical Equipment Co., Ltd., Naor (JO)

( * ) Notice: Subject to any disclaimer, the term of this patent is extended or adjusted under 35 U.S.C. 154(b) by 0 days.

(21) Appl. No.: 09/325,876

(22) Filed: Jun. 4, 1999

(51) Int. Cl.[7] ............... C07D 487/04; A61K 31/519; A61P 15/10
(52) U.S. Cl. .................. 514/234.5; 514/252.16; 514/258; 544/118; 544/262
(58) Field of Search .................. 544/262, 118; 514/234.2, 252.16, 258

(56) References Cited

FOREIGN PATENT DOCUMENTS

| | | |
|---|---|---|
| 0 911 333 A1 | 4/1999 | (EP) . |
| WO 94/28902 | 12/1994 | (WO) . |
| WO 98/49166 | 11/1998 | (WO) . |
| WO 99/54333 | 10/1999 | (WO) . |

OTHER PUBLICATIONS

Pyrazolodiazepines, 1,3–(and 2,3–) Dialkyl–4, 6–dihydro–8–arylpyrazolo [4,3–e] [1,4]diazepin–5–ones as Antianxiety Agents), Horace A. Dewald, et al., J. of Med. Chem., 1973, vol. 16, No. 12, pp. 1346–1354.

Potential Antipsychotic Agents. 7. Synthesis and Antidopaminergic Properties of the Atypical High Potent (S)–5–Bromo–2,3–dimethoxy–N– [(1–ethyl–2–pyrrolidinyl)methyl]benzamide and Related Compounds. A Comparative Study, Thomas Högberg et al., J. Med. Chem. 1990, 33, 2305–2309.

Nucleophilic Annulations of Aromatics, Nvel Route to Benzo–Fused Ring Systems via Oxazoline Activation, A. I. Meyers et al., J. Org. Chem., 1981, 46, 783–788.

Effects of Eurycoma longifolia Jack on Penile Erection Index and Homosexual Mounting in Rats, H.H. Ang et al., Pharmaceutical Sciences 1997, 3: 117–119.

"The Condensed Chemical Dictionary, Ninth Ed." Gesser G. Hawley, Van Nostrand, New York, 1977, pp. 27 and 650.*

Andrew Streitwieser, Jr. and Clayton H. Heathcock, "Introduction to Organic Chemistry 2nd Ed.", Macmillan New York, 1981, p. 753.*

John D. Roberts and Marjorie C. Caserio, "Basic Principles of Organic Chemistry", Benjamin, New York, 1964.*

C. David Gutsche "The Chemistry of Carbonyl Compounds", Prentice–Hall, Englewood Cliffs, NJ, p 46–47. 1965.*

"The Aldrich Catalog", Aldrich Chemical Company, Milwaukee, 1992, p 1138.*

* cited by examiner

*Primary Examiner*—Mukund J. Shah
*Assistant Examiner*—Thomas McKenzie
(74) *Attorney, Agent, or Firm*—Finnegan, Henderson, Farabow, Garrett & Dunner, L.L.P.

(57) ABSTRACT

The present invention relates to novel compounds and pharmaceutical compositions containing the same. The disclosed compounds are useful for treatment of inter alia erectile dysfunction. They are comprised by the general formula (I);

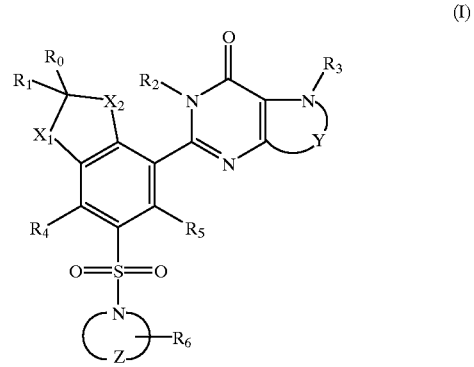

18 Claims, 2 Drawing Sheets

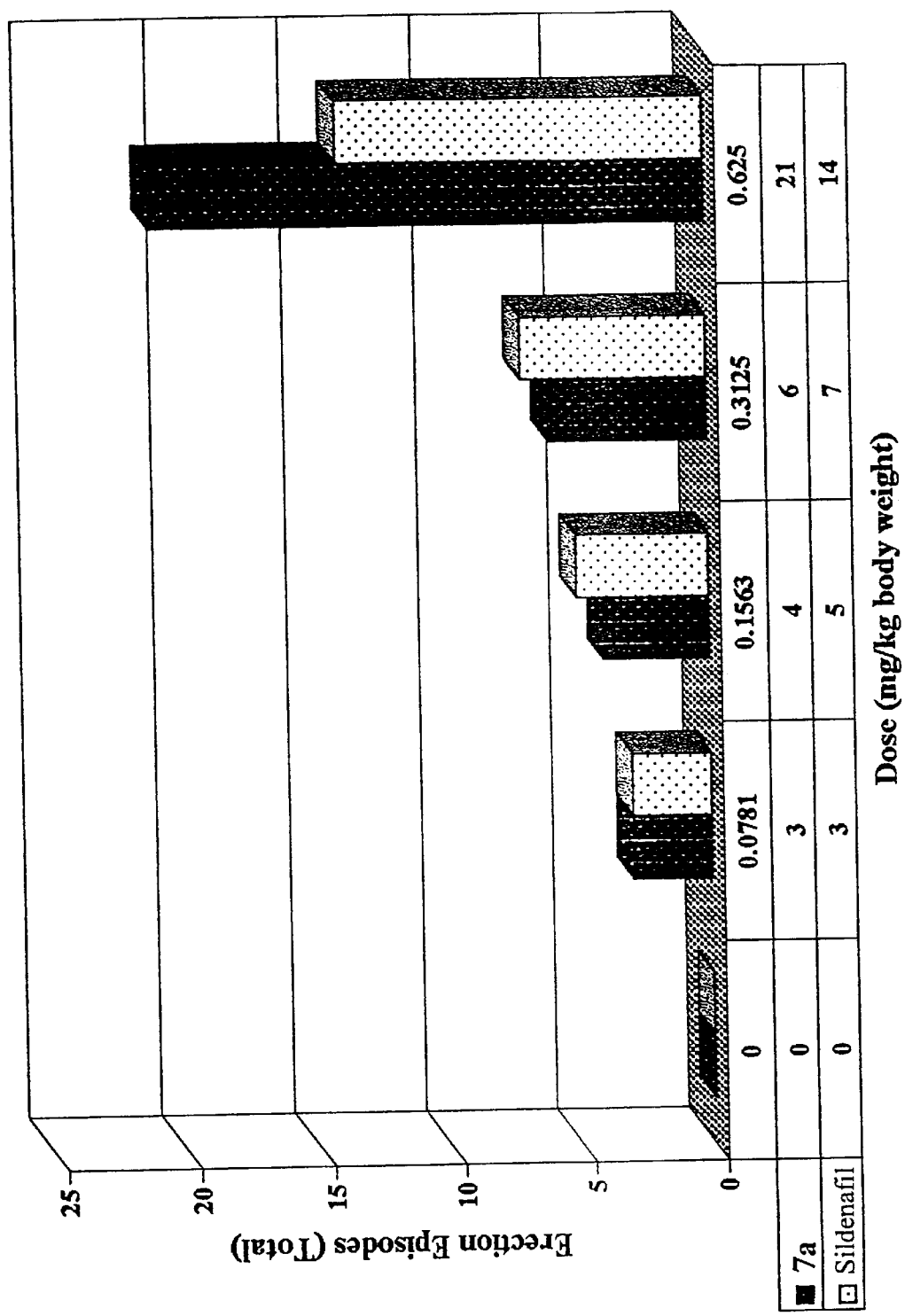
Fig. 1; Total number of erection episodes for 7a and sildenafil.

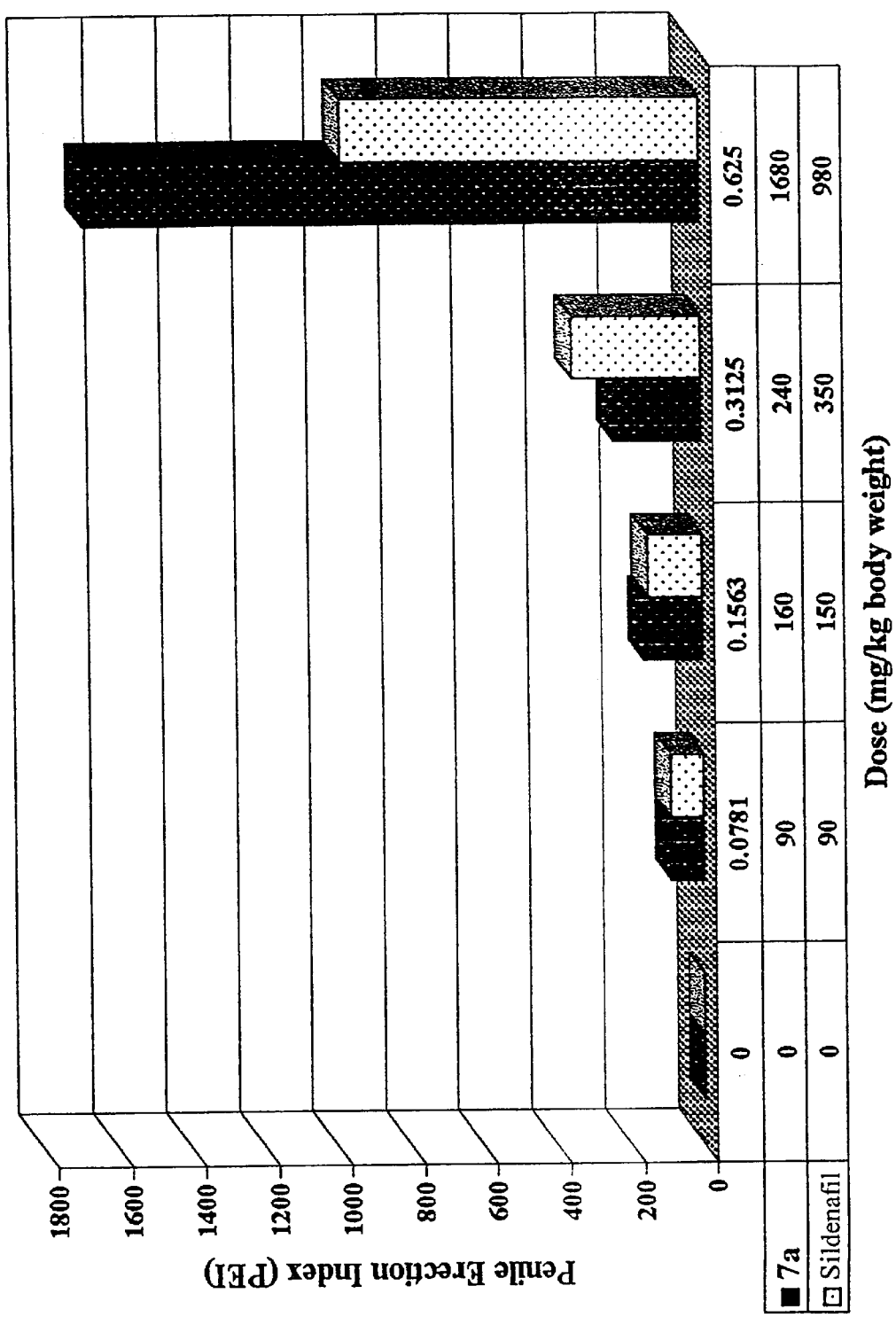
Fig. 2; Penile erection index for 7a and sildenafil.

COMPOUNDS AND PHARMACEUTICAL COMPOSITIONS CONTAINING THE SAME

FIELD OF THE INVENTION

The present invention relates to novel compounds, pharmaceutical compositions containing the same as well as a method for treatment of erectile dysfunction, wherein said compounds are administered.

BACKGROUND OF THE INVENTION

Erectile dysfunction is a disorder which is very common throughout the world. The recent introduction of sildenafil (the active ingredient in Viagra®) has improved the possibilities of treating this disorder significantly. Sildenafil and compounds closely related thereto are disclosed in EP 463 756, EP 702 555 and WO 98/49166 (all to Pfizer Ltd.).

However, despite the useful therapeutic properties of sildenafil, not all patients are successfully treated with this agent. Thus, there is still a great need in the art for compounds having improved therapeutic properties compared to sildenafil.

DISCLOSURE OF THE INVENTION

There are now provided novel compounds with surprisingly improved therapeutic efficiency in comparison with the prior art cited above. In summary, the present invention relates to a compound having the general formula (I):

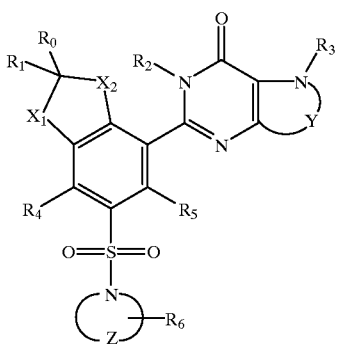

(I)

wherein $R_0$–$R_6$ are independently selected from at least one of a group of substituents (a)–(g) consisting of:

(a) H;
(b) straight chain, branched or cyclic saturated or unsaturated alkyl or hydroxyalkyl having 1–6 carbon atoms;
(c) O-alkyl, S-alkyl or N-(alkyl)$_n$ where alkyl is as defined in (b) and n is 1 or 2;
(d) C(O)-alkyl, O—C(O)-alkyl, S—C(O)-alkyl or NH—C(O)-alkyl, where alkyl is as defined in (b);
(e) F, Cl or Br;
(f) O-aryl;
(g) $NR_8R_9$, wherein $R_8$ and $R_9$ independently is H or straight chain, branched or cyclic saturated or unsaturated alkyl, C(O)-alkyl, hydroxyalkyl or O-alkyl having 1–6 carbons atoms; wherein $NR_8R_9$ optionally may form a five- or six-membered saturated or unsaturated ring;

wherein $X_1$ and $X_2$ are independently selected from a group of radicals consisting of:

—$C_m$— independently substituted with the substituents (a)–(g), where m is an integer from 1 to 3 and the radical —$C_m$— optionally may contain a double bond, ketone or thioketone functionality;

—O—;

—S—; and

—$NR_{10}$—, where $R_{10}$ is H or straight chain, branched or cyclic saturated or unsaturated alkyl, C(O)-alkyl, hydroxyalkyl or O-alkyl having 1–6 carbons atoms;

wherein Y is selected from a group of radicals consisting of:

—$CR_{11}$=N—; —N=$CR_{12}$—; —N=N—;
—$CR_{13}$=$CR_{14}$—; —$CR_{15}R_{16}CR_{17}R_{18}$—;
—$CR_{19}R_{20}$O—; —$OCR_{21}R_{22}$—; —$CR_{22}R_{23}NR_{24}$—;
—$NR_{25}CR_{26}R_{27}$— and —$NR_{28}NR_{29}$—, where $R_{11}$–$R_{29}$ are independently selected from the substituents (a)–(g);

wherein z taken together with the nitrogen atom to which it is attached forms a group selected from pyrrolidinyl, piperidinyl, morpholinyl, imidazolyl, pyridinyl, pyrrolyl and 4-N-($R_{30}$)-piperazinyl, whereby $R_{30}$ is selected from the substituents (a)–(g);

tautomers, solvates and radiolabelled derivatives thereof; and pharmaceutically acceptable salts thereof.

As examples of pharmaceutically acceptable salts mention can be made of acid addition salts, e.g. a salt formed by reaction with hydrohalogen acids, such as hydrochloric acid, sulphuric acid, phosphoric acid, nitric acid, aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halogenbensensulphonic acid, toluenesulphonic acid and naphtalenesulphonic acid.

In a preferred embodiment of the present invention, Y is —$CR_{11}$=N—. $R_{11}$ is preferably an n-propyl group.

Furthermore, it is preferred that Z taken together with the nitrogen atom to which it is attached forms a 4-N-($R_{30}$)-piperazinyl group. Preferably, $R_{30}$ is a methyl group.

Moreover, it is preferred that $X_1$ is —$C_m$—. Preferably, m is 1. Most preferably, $X_1$ is —$CH_2$—.

It is preferred that $X_2$ is —O—.

In a more preferred embodiment of the present invention, $R_2$ is H.

In an even more preferred embodiment, $R_3$ is a methyl group.

In a still even more preferred embodiment, $R_4$, $R_5$ and $R_6$ are all H.

In the most preferred embodiment of the present invention, said compound is 5-[2,3-dihydro-5-(4-methylpiperazin-1-ylsulfonyl)-7-benzofuryl]-1-methyl-3-propyl-6,7-dihydro-1H-pyrazolo[4,3-d]pyrimidin-7-one, the structure of which is depicted hereinbelow. This compound is hereinafter denoted 7a.

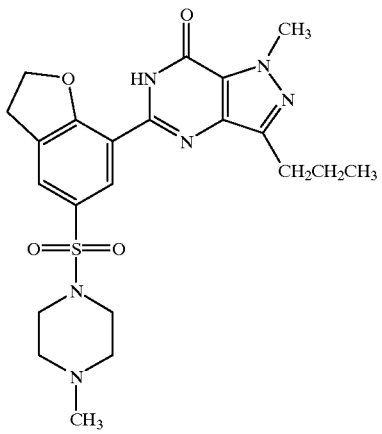

Furthermore, the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, intraperitoneal, nasal, buccal, sublingual or subcutaneous administration or for administration via the respiratory tract in the form of e.g. an aerosol or an air-suspended fine powder. Thus, the composition may be in the form of e.g. tablets, capsules, powders, micro-particles, granules, syrups, suspensions, solutions, transdermal patches or suppositories.

It should be noted that the composition according to the present invention may optionally include two or more of the above outlined compounds.

In addition, the present invention relates to a method for treatment of erectile dysfunction, wherein said method comprises administering to an animal, including human, patient of a therapeutically effective amount of a compound as outlined above.

Furthermore, it is also anticipated that the compounds according to the present invention have beneficial platelet anti-aggregatory, anti-vasospastic and vasodilatory activity. Thus, they should be useful in the treatment of a number of disorders, such as angina, hypertension, congestive heart failure, peripheral vascular disease, atherosclerosis, stroke, bronchitis, asthma, allergic rhinitis and glaucoma.

The typical dosage of the compounds according to the present invention varies within a wide range and will depend on various factors such as the individual requirement of each patient and the route of administration. The dosage is generally within the range of 0.01–100 mg/kg body weight.

The general synthetic pathway to formula (I) may be summarized as shown below (Δ=heat):

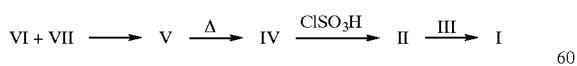

Thus, the present invention also relates to a process for the preparation of a compound as set forth above, wherein a compound having the general formula (II) is reacted with a compound having the general formula (III), optionally in the presence of a solvent, wherein $R_0$–$R_6$ and X–Z are as defined above.

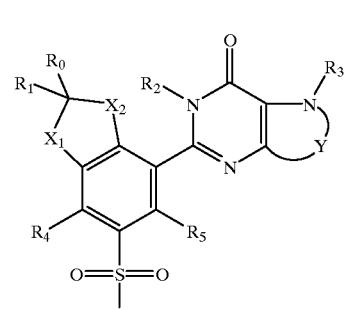

(II)

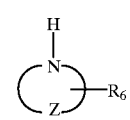

(III)

The compound (II) is prepared by reacting a compound having the general formula (IV) with ClSO$_3$H, optionally in the presence of a solvent.

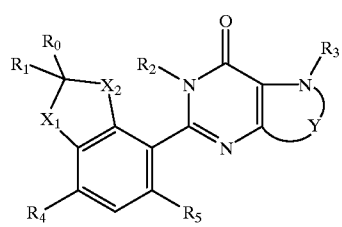

(IV)

The compound (IV) is prepared by heating a compound having the general formula (V) under basic conditions, optionally in the presence of a solvent.

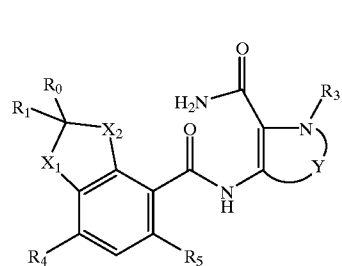

(V)

The compound (V) is prepared by reacting a compound having the general formula (VI) with a compound having the general formula (VII), optionally in the presence of a solvent and a base.

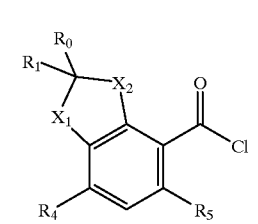

(VI)

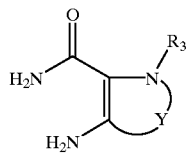

(VII)

As for the selection of e.g. suitable reaction and purification conditions, useful guidance is also provided by the following publications, which are incorporated herein by reference:

DeWald, H. A., Nordin, I. C., L'Italien, Y. J., Parcell, R. F., *J. Med. Chem.*, 16, 1346–1354 (1973);

Meyers, A. I., Reuman, M., Gabel., R. A., *J. Org. Chem.*, 46, 783–788 (1981);

Högberg, T., de Paulis, T., Johansson, L., Kumar, Y., Hall,. H., Ögren, S. O., *J. Med. Chem.*, 33, 2305–2309 (1990).

By guidance of known reference literature, the synthesis of the starting substances (VI) and (VII) is readily accomplished by a person skilled in the art.

The present invention is further illustrated by the following non-limiting experimental part.

BRIEF DESCRIPTION OF THE DRAWINGS

FIG. 1 shows a comparative study of total erection episodes as a function of dose for rats treated with 7a and sildenafil, respectively.

FIG. 2 shows a comparative study of penile erection index as a function of dose for rats treated with 7a and sildenafil, respectively.

PREPARATION OF THE COMPOUNDS OF THE PRESENT INVENTION

Instruments used for analysis:

The melting points (m.p.) were determined on an electrothermal Mel-Temp. apparatus. They are uncorrected. $^1$H and $^{13}$C NMR spectra were recorded on a Bruker-WM 400 or -DPX 300 MHz spectrometer, with tetramethylsilane (TMS) as internal reference. Electron impact (EI) mass spectra were obtained using a Finnigan 731 spectrometer at 70 eV. Elemental analyses were performed at the Microanalytical Laboratory of the Chemistry Department, Al-Najah National University, West Bank.

EXAMPLE 1

Preparation of Compound 4

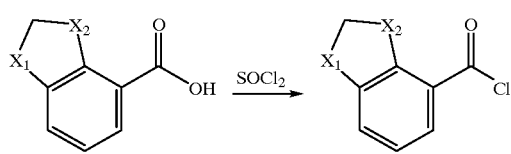

(1; $X_1$ and $X_2$ are as outlined above)     (2)

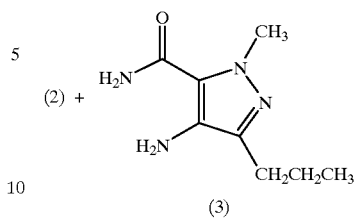

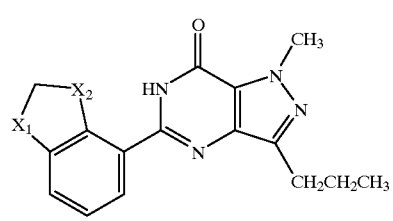

Compound 4 was prepared by treating 1 (0.1 mole) with $SOCl_2$ in a conventional manner yielding 2, which was then refluxed with 3 in benzene (100 ml) and $NEt_3$ (30 ml) for 2–3 h. The benzene was distilled off, and the solid product 4 was collected, washed with $H_2O$, dried and recrystallized from a suitable solvent. Yield: 82–93%.

EXAMPLE 2

Preparation of Compound 5

(5)

Potassium t-butoxide (0.01 mole) was added to a stirred suspension of 4 (0.01 mole) in t-BuOH (60 ml), and the resulting mixture was refluxed for 8 h. Water (40 ml) was then added, after which the solution was neutralized with diluted HCl (aq; 4%) to pH 7 and cooled. The solid product 5 was collected, washed with cold $H_2O$ and recrystallized from a suitable solvent. The yield was 86–95%.

EXAMPLE 3

Preparation of Compound 6

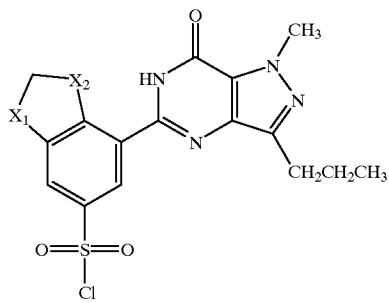
(6)

Compound 5 (0.006 mole) was added in portions to chlorosulfonic acid (4 ml) cooled to 0° C. under stirring. The temperature of the reaction mixture was then allowed to rise to 25° C., followed by heating to 65–70° C. for 1 h. The reaction mixture was subsequently poured onto crushed ice (50 g), after which the precipitated solid product 6 was collected and used directly in the next reaction step. Yield: 82–91%.

EXAMPLE 4

Preparation of Compound 7

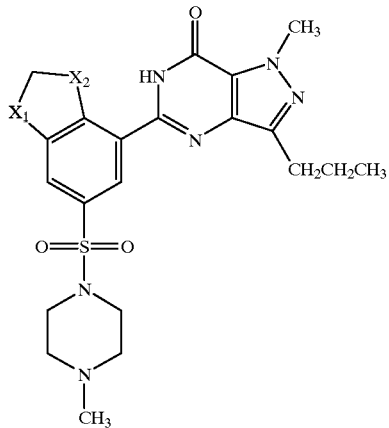
(7)

Compound 6 (0.005 mole) dissolved in THF (20 ml) was added to a solution of 1-methylpiperazine (2 ml) in THF (20 ml). The resulting mixture was stirred for 1 h at 20–25° C. The THF was distilled off, and the residue was treated with cold $H_2O$. The resulting white solid product 7 was collected, washed with $H_2O$, drained and recrystallized from a suitable solvent. Yield: 80–88%.

By following the reaction protocol above, the compounds 7a–7l listed in Table 1 below were prepared.

TABLE 1

Compounds prepared, where $X_1$ is as specified and $X_2$ is —O— for all the compounds.

| Compound | $X_1$ |
|---|---|
| 7a | $CH_2$ |
| 7b | O |
| 7c | S |
| 7d | $NCH_3$ |
| 7e | $NC_2H_5$ |
| 7f | $NCH(CH_3)_2$ |
| 7g | $NC(O)CH_3$ |
| 7h | $NC(O)NHPh$ |
| 7i | $NC(S)NHPh$ |
| 7j[i)] | C=O |
| 7k[i)] | C=S |
| 7l[ii)] | NH | i) The compounds 7j and 7k were obtained after protection/deprotection of a 3-keto/thioketo group in the corresponding compounds 2j and 2k.

ii) Compound 7l was obtained from 7g by selective hydrolysis in 15% HCl for 20 min with heating.

EXAMPLE 5

Detailed Preparation and Physical Properties of 7a and its Precursors

Preparation of 4-(2,3-dihydro-7-benzofurylamino)-1-methyl-3-propyl-5-pyrazole-carboxamide (4a, i.e. 4 wherein $X_1$=$CH_2$ and $X_2$=O):

A mixture of 2,3-dihydrobenzofuran-7-carboxylic acid (1.5 g, 0.0091 mole) and $SOCl_2$ (8 ml) was refluxed (oil bath) for 3 h. Excess of $SOCl_2$ was removed in vacuo, and the residual acid chloride was treated with a solution of compound 1 (1.4 g, 0.0077 mole) in anhydrous benzene (25 ml), followed by addition of $NEt_3$ (3 ml). The solid residue was soaked in cold water (40 ml), and the remaining solid product was collected by suction filtration, drained, washed with water (2×20 ml) and diethyl ether (2×10 ml) and dried, thereby yielding 4a.

Product yield=2.3 g (91%);

M.p.=173–174° C.;

Elemental analysis=Calculated for $C_{17}H_{20}N_4O_3$ (MW=328.37). C 62.18, H 6.14, N 17.06%. Found C 61.95, H 6.07, N 17.11%.

$^1$H NMR ($CDCl_3$): δ 0.86 (t, J=7.4 Hz, 3H, $CH_2CH_2C\underline{H}_3$), 1.56 (m, 2H, $CH_2C\underline{H}_2CH_3$), 2.46 (t, J=7.6 Hz, 2H, $C\underline{H}_2CH_2CH_3$), 3.27 (t, J=8.5 Hz, 2H, C3'-H), 3.97 (s, 3H, N—$C\underline{H}_3$), 4.73 (t, J=8.5 Hz, 2H, C2'-H), 6.94 (t, J=7.6 Hz, 1H, C5'-H), 7.34 (d, J=7.2 Hz, 1H, C4'-H), 6.26, 7.72 (2 br s, 1H each of $CON\underline{H}_2$), 7.86 (d, J=8.1 Hz, 1H, C6'-H), 8.88 (br s, 1H, N$\underline{H}$CO).

$^{13}$C NMR ($CDCl_3$): δ 13.7 ($CH_2CH_2\underline{C}H_3$), 22.2 ($CH_2\underline{C}H_2CH_3$), 27.5 ($\underline{C}H_2CH_2CH_3$), 28.9 (C-3'), 39.1 (N—$\underline{C}H_3$), 72.8 (C-2'), 114.5 (C-3), 115.6 (C-7'), 121.4 (C-5'), 128.0 (C-3'a), 129.35, 129.34 (C-4' and C-6'), 132.1 (C-4), 147.0 (C-5), 157.9 (C-7'a), 161.7 (NH$\underline{C}$O), 165.8 ($\underline{C}ONH_2$).

Preparation of 5-(2,3-dihydro-7-benzofuryl)-1-methyl-3-propyl-6,7-dihydro-1H-pyrazolo[4,3-d]pyrimidine-7-one (5a)

Potassium t-butoxide (0.5 g, 0.0045 mole) was added to a stirred suspension of compound 4a (1.1 g, 0.0034 mole) in t-butanol (20 ml), and the resulting mixture was heated under reflux (oil bath) for 8 h and then allowed to cool to room temperature. Water (14 ml) was added, after which the solution was neutralized with HCl (aq; 4%; 13 ml) to pH 7, cooled to about 5–10° C., collected by suction filtration, washed with cold water (2×10 ml), crystallized from ethanol and dried, thereby yielding 5a.

Product yield=1.0 g (96%);

M.p.=176–178° C. (decomposition);

Elemental analysis=Calculated for $C_{17}H_{18}N_4O_2$ (MW=310.36) C 65.79, H 5.85, N 18.05%. Found C 65.72, H 5.91, N 17.93%.

$^1$H NMR (CDCl$_3$): δ 0.99 (t, J=7.4 Hz, 3H, CH$_2$CH$_2$C$\underline{H}_3$), 1.82 (m, 2H, CH$_2$C$\underline{H}_2$CH$_3$), 2.86 (t, J=7.6 Hz, 2H, C$\underline{H}_2$CH$_2$CH$_3$), 3.22 (t, J=8.1 Hz, 2H, C3'-H), 4.19 (s, 3H, N—C$\underline{H}_3$), 4.73 (t, J=8.1 Hz, 2H, C2'-H), 6.94 (t, J=7.6 Hz, 1H, C5'-H), 7.22 (d, J=7.2 Hz, 1H, C4'-H), 8.16 (d, J=8.1 Hz, 1H, C6'-H), 10.69 (br s, 1H, N6-H).

$^{13}$C NMR (CDCl$_3$): δ 14.0 (CH$_2$CH$_2$$\underline{C}$H$_3$), 22.2 (CH$_2$$\underline{C}$H$_2$CH$_3$), 27.7 ($\underline{C}$H$_2$CH$_2$CH$_3$), 28.9 (C-3'), 38.1 (N—$\underline{C}$H$_3$), 72.6 (C-2'), 114.5 (C-3), 121.6 (C-5'), 124.4 (C-7'), 127.3, 127.5 (C-4' and C-6'), 128.1 (C-3'a), 138.5 (C-3a), 146.4 (C-5), 146.7 (C-7a), 154.0 (C-7), 156.8 (C-7'a).

Preparation of 5-(2,3-dihydro-5-chlorosulfonyl-7-benzofuryl)-1-methyl-3-propyl-6,7-dihydro-1H-pyrazolo[4,3-d]pyrimidin-7-one (6a)

Compound 5a (0.95 g, 0.003 mole) was added in portions to chlorosulfonic acid (2 ml) cooled to 0° C. (ice-bath) under stirring. The resulting yellow solution was then allowed to attain room temperature and was subsequently slowly heated to 65–70° C. (oil bath) for 1 h. The reaction mixture was then slowly poured onto crushed ice (25 g), whereby a white solid precipitated immediately. The white solid was filtered, dried and recrystallized from THF/petroleum ether (b.p. 40–60° C.), thereby yielding 6a.

Product yield=1.04 g (84%);

M.p.=221–222° C.

No elemental analysis was performed on 6a ($C_{17}H_{17}ClN_4O_4S$; MW=408.86).

[M]$^+$=408/410 (3:1 ratio; Cl isotopic peaks);

The crude product 6a (92% yield; m.p. 216–218° C.) can be used directly in the next reaction step.

Preparation of 5-[2,3-dihydro-5-(4-methylpiperazin-1-ylsulfonyl)-7-benzofuryl]-1-methyl-3-propyl-6,7-dihydro-1H-pyrazolo[4,3-d]pyrimidin-7-one (7a)

Compound 6a (1.25 g, 0.003 mole) was dissolved in THF (10 ml) and added to a solution of 1-methylpiperazine (1 ml) in THF (10 ml). The resulting mixture was stirred at room temperature for 1 h. The THF was then removed in vacuo, and the residue was treated with cold water (50 ml). The resulting white precipitate was filtered under suction, washed with water (2×10 ml), drained and recrystallized from 90% ethanol, thereby yielding 7a.

Product yield=1.2 g (83%);

M.p.=194–195° C.;

Elemental analysis=Calculated for $C_{22}H_{28}N_6O_4S$ (MW=472.57) C 55.92, H 5.97, N 17.78, S 6.79%. Found C 56.00, H 6.09, N 17.51, S 6.73%.

$^1$H NMR (CDCl$_3$): δ 0.96 (t, J=7.2 Hz, 3H, CH$_2$CH$_2$C$\underline{H}_3$), 1.79 (m, 2H, CH$_2$C$\underline{H}_2$CH$_3$), 2.20 (s, 3H, N4"-C$\underline{H}_3$), 2.43 (br s, 4H, C3"-H/C5"-H), 2.85 (t, J=7.2 Hz, 2H, C$\underline{H}_2$CH$_2$CH$_3$), 3.01 (br s, 4H, C2"-H/C6"-H), 3.32 (t, J=8.5 Hz, 2H, C3'-H), 4.17 (s, 3H, N1-C$\underline{H}_3$), 4.89 (t, J=8.5 Hz, 2H, C2'-H), 7.56 (s, 1H, C4'-H), 8.54 (s, 1H, C6'-H), 10.49 (br s, 1H, N6-H).

$^{13}$C NMR (CDCl$_3$): δ 13.9 (CH$_2$CH$_2$$\underline{C}$H$_3$), 22.1 (CH$_2$$\underline{C}$H$_2$CH$_3$), 27.5 ($\underline{C}$H$_2$CH$_2$CH$_3$), 28.4 (C-3'), 38.1 (N—$\underline{C}$H$_3$), 45.6 (N4"-$\underline{C}$H$_3$), 45.9 (C-3"/C-5"), 53.9 (C-2"/C-6"), 74.0 (C-2'), 114.5 (C-3), 124.4 (C-7'), 126.2 (C-4'), 128.5 (C-6'), 129.1 (C-5'), 130.2 (C-3'a), 138.1 (C-3a), 145.2 (C-5), 146.7 (C-7a), 153.6 (C-7), 159.9 (C-7'a).

Animal Experiments Involving Compound 7a

The purpose of this study was to compare the biological activity of compound 7a with that of sildenafil. In particular, the respective ED$_{50}$-value (ED=effective dose), erection episodes and penile erection indices of said compounds in the treatment of male rats were determined. The penile erection index is an established means of determining the erection promoting properties of a substance (see e.g. Ang, H. H., Sim, M. K., Pharm. Sci., 3, 117–119 (1997) and references cited therein).

In these experiments, the compounds 7a and sildenafil were administered to male rats orally. The doses used for both drugs were 0.0781, 0.1562, 0.3125 and 0.625 mg/kg body weight. Sildenafil was dissolved in distilled water, whereas 7a was dissolved in 1% HCl solution (aq). Control animals were administered with the vehicles only, i.e. distilled water or the 1% HCl solution. During the experiments, the rats were placed in glass cages for observation and had access to food and water. During 2 h after administration of the investigated compounds, the penile erection of the rats was monitored. It is worth mentioning that no copulation mounting behaviour was observed in these experiments.

The number of rats responding to this experiment protocol was recorded, and the ED$_{50}$ results are shown in Table 2.

TABLE 2

Study of number (#) and percentage response as a function of dose for rats subjected to 7a and sildenafil, respectively.

| Dose[i] | # Rats | 7a; responding rats[ii] | | Sildenafil; responding rats[iii] | |
|---|---|---|---|---|---|
| (mg/kg) | tested | # | % | # | % |
| 0.0781 | 10 | 3 | 30 | 3 | 30 |
| 0.1562 | 10 | 4 | 40 | 3 | 30 |
| 0.3125 | 10 | 4 | 40 | 5 | 50 |
| 0.6250 | 10 | 8 | 80 | 7 | 70 |

[i]No rats responded when distilled water or 1% HCl was administered.
[ii]Calculated ED$_{50}$ = 0.2473 mg/kg body weight;
[iii]Calculated ED$_{50}$ = 0.2843 mg/kg body weight; where the ED$_{50}$ values are significantly different with a 95% confidence interval.

As is clear from Table 2, the ED$_{50}$ value of 7a is lower than that of sildenafil. Thus, a lower dose of 7a as compared to sildenafil is required in order to elicit an erectile response.

Furthermore, as for the intensity of the erectile response per se, the observed number of erection episodes and calculated penile erection indices substantiate that the compound 7a is superior to sildenafil, especially at higher doses. The total number of observed erection episodes and the calculated penile erection indices are depicted in FIGS. 1 and 2, respectively.

Moreover, according to preliminary toxicity studies in rats, the compound 7a is tolerated up to a dose of about 35 mg/100 kg body weight without any detrimental effects. The compound 7a appears to be completely non-toxic and free from undesirable side-effects. Thus, high doses of 7a provide a particularly efficient means for treatment of erectile dysfunction.

In summary, it should be clear from the present disclosure that the compounds according to the present invention are versatile new pharmaceutically active agents for the treatment of erectile dysfunction.

What is claimed is:

1. A compound having the formula (I):

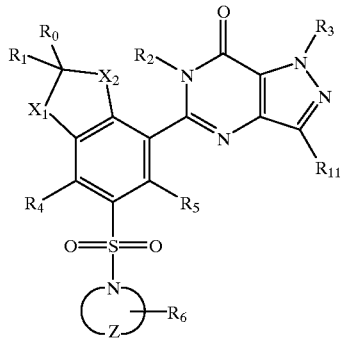

(I)

wherein $R_0$–$R_6$ are independently selected from at least one of a group of substituents (a)–(g) consisting of:
(a) H;
(b) straight or branched chain alkyl or hydroxyalkyl having up to 6 carbon atoms;
(c) O-alkyl, S-alkyl or N-(alkyl)$_n$, where alkyl is as defined in (b) and n is 1 or 2,;
(d) C(O)-alkyl, O—C(O)-alkyl, S—C(O)-alkyl or NH—C(O)-alkyl, where alkyl is as defined in (b);
(e) F, Cl or Br;
(f) O-aryl;
(g) $NR_8R_9$, wherein $R_8$ and $R_9$ independently is H or straight or branched chain alkyl, C(O)-alkyl, hydroxyalkyl or O-alkyl having up to 6 carbon atoms;
wherein $X_1$ and $X_2$ are independently selected from a group of radicals consisting of:
—$C_m$— independently substituted with the substituents (a)–(g), where m is an integer from 1 to 3 and the radical —$C_m$— optionally may contain a double bond or ketone functionality;
—O—; and
—S—;
wherein $R_{11}$ is selected from the substituents (a)–(g);
wherein Z taken together with the nitrogen atom to which it is attached forms a group selected from pyrrolidinyl, piperidinyl, morpholinyl and 4-N-($R_{30}$)-piperazinyl, wherein $R_{30}$ is selected from the substituents (a)–(g);
tautomers and solvates thereof; and
pharmaceutically acceptable salts thereof.

2. A compound according to claim 1, wherein $R_{11}$ is n-propyl group.

3. A compound according to claim 1, wherein Z taken together with the nitrogen atom to which it is attached forms a 4-N-($R_{30}$)-piperazinyl group.

4. A compound according to claim 3, wherein $R_{30}$ is a methyl group.

5. A compound according to claim 1, wherein $X_1$ is —$C_m$—.

6. A compound according to claim 5, wherein m is 1.

7. A compound according to claim 6, wherein $X_1$ is —$CH_2$—.

8. A compound according to claim 1, wherein $X_2$ is —O—.

9. A compound according to claim 1, wherein $R_2$ is H.

10. A compound according to claim 9, wherein $R_3$ is a methyl group.

11. A compound according to claim 10, wherein $R_4$, $R_5$ and $R_6$ are H.

12. A compound according to claim 11, wherein said compound is 5-[2,3-dihydro-5-(4-methylpiperazin-1-ylsulfonyl)-7-benzofuryl]-1-methyl-3-propyl-6,7-dihydro-1H-pyrazolo[4,3-d]pyrimidin-7-one.

13. A pharmaceutical composition comprising a compound according to claim 1 as active ingredient in association with a pharmaceutically acceptable adjuvant, diluent or carrier.

14. A process for the preparation of a compound of claim 1 having the formula (I), wherein a compound having the formula (II) is reacted with a compound having the formula (III), optionally in the presence of a solvent,

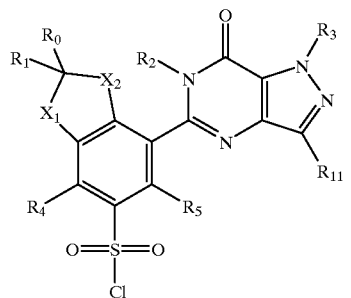

(II)

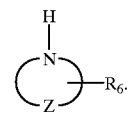

(III)

15. A process according to claim 14, wherein the compound (II) is prepared by reacting a compound having the formula (IV) with $ClSO_3H$, optionally in the presence of a solvent.

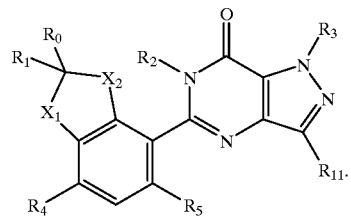

(IV)

16. A process according to claim 15, wherein the compound (IV) is prepared by heating a compound having the formula (V) under basic conditions, optionally in the presence of a solvent.

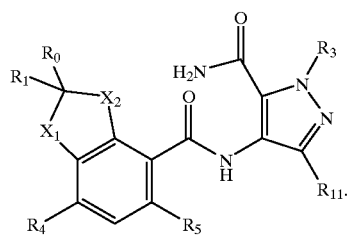

(V)

17. A process according to claim 16, wherein the compound (V) is prepared by reacting a compound having the formula (VI) with a compound having the formula (VII), optionally in the presence of a solvent and a base

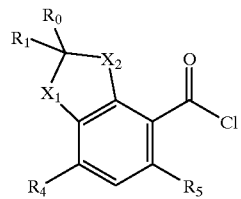

(VI)

-continued

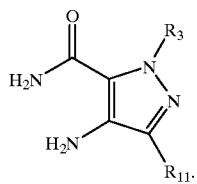

(VII)

18. A method for treatment of erectile dysfunction, wherein said method comprises administering to an animal, including human, patient of a therapeutically effective amount of a compound according to claim 1.

* * * * *